(12) United States Patent
Boutoussov et al.

(10) Patent No.: US 11,883,095 B2
(45) Date of Patent: Jan. 30, 2024

(54) DUAL WAVELENGTH LASER TREATMENT DEVICE

(71) Applicant: Biolase, Inc., Foothill Ranch, CA (US)

(72) Inventors: Dmitri Boutoussov, Dana Point, CA (US); Vladimir Netchitailo, Livermore, CA (US)

(73) Assignee: Biolase, Inc., Foothill Ranch, CA (US)

( * ) Notice: Subject to any disclaimer, the term of this patent is extended or adjusted under 35 U.S.C. 154(b) by 39 days.

(21) Appl. No.: 17/392,807

(22) Filed: Aug. 3, 2021

(65) Prior Publication Data

US 2022/0022961 A1 Jan. 27, 2022

Related U.S. Application Data (60) Continuation of application No. 16/249,829, filed on Jan. 16, 2019, now abandoned, which is a division of
(Continued)

(51) Int. Cl.
*A61B 18/22* (2006.01)
*A61N 5/06* (2006.01)
(Continued)

(52) U.S. Cl.
CPC ............ *A61B 18/22* (2013.01); *A61N 5/0624* (2013.01); *A61B 2018/00577* (2013.01);
(Continued)

(58) Field of Classification Search
CPC .......... A61B 18/22; A61B 2018/00577; A61B 2018/00601; A61B 2018/202;
(Continued)

(56) References Cited

U.S. PATENT DOCUMENTS 4,761,054 A 8/1988 Ishimori et al.
4,930,504 A 6/1990 Diamantopoulos et al.
(Continued)

FOREIGN PATENT DOCUMENTS

CN 1246927 A 3/2000
CN 1543368 A 11/2004
(Continued)

OTHER PUBLICATIONS

Sam's Laser FAQ; Dec. 7, 2013; https://www.repairfaq.org/sam/laserssl.htm#sslint (Year: 2013).
(Continued)

*Primary Examiner* — Jonathan T Kuo
(74) *Attorney, Agent, or Firm* — Greenberg Traurig, LLP (57) ABSTRACT

Embodiments of the invention include a compact, lightweight, hand-held laser treatment device that combines the emissions of two separate laser energy sources into a common optical pathway for improved therapeutic effect. In some embodiments, the device includes a housing having separate first and second laser sources disposed within the interior thereof. In some embodiments, the laser energy emissions from the two internal laser sources can be individually or concurrently transmitted to a delivery tip of the device via a laser transmission path also defined within the interior of the housing. In some embodiments, the structural and functional features of the first and second laser sources, in concert with the unique architecture of the laser transmission path, can be configured to provide efficacy and efficiency in the operation of the device within the spatial constraints of the lightweight, hand-held housing thereof.

18 Claims, 4 Drawing Sheets

Related U.S. Application Data application No. 14/587,955, filed on Dec. 31, 2014, now abandoned.

(60) Provisional application No. 61/922,581, filed on Dec. 31, 2013.

(51) Int. Cl.
*A61B 18/00* (2006.01)
*A61B 18/20* (2006.01)
*A61N 5/067* (2006.01)

(52) U.S. Cl.
CPC ............... *A61B 2018/00601* (2013.01); *A61B 2018/202* (2013.01); *A61B 2018/2065* (2013.01); *A61B 2018/2261* (2013.01); *A61B 2018/2266* (2013.01); *A61B 2018/2272* (2013.01); *A61N 5/067* (2021.08); *A61N 2005/063* (2013.01); *A61N 2005/0644* (2013.01); *A61N 2005/0654* (2013.01); *A61N 2005/0665* (2013.01)

(58) Field of Classification Search
CPC .... A61B 2018/2065; A61B 2018/2261; A61B 2018/2266; A61B 2018/2272; A61N 5/0624; A61N 5/067; A61N 2005/063; A61N 2005/0644; A61N 2005/0654; A61N 2005/0665; A61N 5/0613

See application file for complete search history.

(56) References Cited

U.S. PATENT DOCUMENTS

| | | | |
|---|---|---|---|
| 5,139,494 A | 8/1992 | Freiberg et al. | |
| 5,741,247 A | 4/1998 | Rizoiu et al. | |
| 5,825,958 A | 10/1998 | Gollihar et al. | |
| 6,261,310 B1 * | 7/2001 | Neuberger | A61B 18/20 606/17 |
| 6,592,611 B1 | 7/2003 | Zawada | |
| 6,613,042 B1 | 9/2003 | Tankovich et al. | |
| 6,746,473 B2 | 6/2004 | Shanks | |
| 6,813,289 B2 | 11/2004 | Gruzdev | |
| 7,118,588 B2 | 10/2006 | Tucek | |
| 7,298,767 B2 | 11/2007 | Gruzdev | |
| 7,548,568 B2 | 6/2009 | Gruzdev | |
| 7,702,196 B2 | 4/2010 | Boutoussov | |
| 7,922,751 B2 | 4/2011 | Shanks | |
| 7,947,067 B2 | 5/2011 | Tucek | |
| 8,083,785 B2 | 12/2011 | Tucek | |
| 8,439,959 B2 | 5/2013 | Tucek | |
| 8,485,818 B2 | 7/2013 | Boutoussov | |
| 8,679,103 B2 | 3/2014 | Krespi | |
| 9,433,475 B2 * | 9/2016 | Bierbaum | A61B 18/22 |
| 2002/0111610 A1 | 8/2002 | Nordquist | |
| 2002/0123781 A1 | 9/2002 | Shanks et al. | |
| 2002/0138072 A1 * | 9/2002 | Black | A61B 18/22 606/17 |
| 2003/0021312 A1 | 1/2003 | Gruzdev | |
| 2003/0036680 A1 | 2/2003 | Black | |
| 2003/0018324 A1 | 4/2003 | Davenport et al. | |
| 2003/0216719 A1 | 11/2003 | Debenedictis et al. | |
| 2004/0006378 A1 | 1/2004 | Shanks | |
| 2004/0097910 A1 * | 5/2004 | Brugger | A61C 1/088 606/18 |
| 2004/0133191 A1 | 7/2004 | Momiuchi et al. | |
| 2004/0158301 A1 | 8/2004 | Tucek | |
| 2005/0085802 A1 | 4/2005 | Gruzdev | |
| 2005/0131499 A1 | 6/2005 | Shanks | |
| 2006/0064080 A1 * | 3/2006 | Cao | A61B 18/22 607/93 |
| 2006/0095099 A1 | 5/2006 | Shanks | |
| 2006/0206176 A1 | 9/2006 | Shanks | |
| 2006/0224218 A1 | 10/2006 | Tucek | |
| 2006/0229690 A1 | 10/2006 | Shanks | |
| 2007/0135870 A1 | 6/2007 | Shanks | |
| 2007/0250137 A1 | 10/2007 | Daffer | |
| 2008/0043790 A1 | 2/2008 | Gruzdev | |
| 2008/0077198 A1 | 3/2008 | Webb et al. | |
| 2008/0262577 A1 | 10/2008 | Altshuler et al. | |
| 2009/0257465 A1 | 10/2009 | Gruzdev | |
| 2009/0275032 A1 | 11/2009 | Zelickson et al. | |
| 2009/0275932 A1 * | 11/2009 | Zelickson | A61B 18/22 606/15 |
| 2010/0016931 A1 | 1/2010 | Shanks | |
| 2010/0151406 A1 | 6/2010 | Boutoussov et al. | |
| 2010/0160838 A1 | 6/2010 | Krespi | |
| 2010/0216088 A1 * | 8/2010 | Bierbaum | A61B 18/22 433/29 |
| 2010/0324426 A1 | 12/2010 | Tucek | |
| 2011/0087312 A1 | 4/2011 | Shanks | |
| 2011/0208274 A1 | 8/2011 | Bornstein | |
| 2011/0305250 A1 | 12/2011 | Chann et al. | |
| 2013/0304164 A1 | 11/2013 | Zanata et al. | |

FOREIGN PATENT DOCUMENTS

| | | |
|---|---|---|
| CN | 1891173 A | 1/2007 |
| CN | 101484082 A | 7/2009 |
| EP | 1958584 A1 | 8/2008 |
| WO | 199816855 A1 | 4/1998 |
| WO | 2003017670 A1 | 2/2003 |
| WO | 2007103158 A2 | 9/2007 |

OTHER PUBLICATIONS

International Search Report for International Application No. PCT/US2014/073056, dated Apr. 30, 2015, 5 pages.
Written Opinion for International Application No. PCT/US2014/073056, dated Apr. 30, 2015, 5 pages.

* cited by examiner

DUAL WAVELENGTH LASER TREATMENT DEVICE

CROSS-REFERENCE TO RELATED APPLICATIONS

This application is a continuation of U.S. application Ser. No. 16/249,829, filed Jan. 16, 2019, entitled "Dual Wavelength Laser Treatment Device," which is a divisional application of U.S. application Ser. No. 14/587,955 entitled "Dual Wavelength Laser Treatment Device", filed Dec. 31, 2014, which claims the benefit and priority of U.S. Provisional Application No. 61/922,581 entitled "Dual Wavelength Laser Treatment Device", filed on Dec. 31, 2013, the entire contents of which are incorporated herein by reference.

BACKGROUND OF THE INVENTION

1. Field of the Invention

Some embodiments of the invention relate generally to medical laser systems. Some embodiments relate to a compact and lightweight hand-held laser treatment device that combines the emissions of two or more separate laser energy sources into a common optical pathway for improved therapeutic effect.

2. Description of Art

Lasers find application in a variety of medical and dental treatment procedures, with some of the most common operations involving the cutting, ablation, disinfection or other treatment of tissue. Depending on the particular wavelength, output power, and pulse width of the laser emission, as well as the absorptivity of the target tissue, varying biological materials from soft tissue such as muscles and skin, to hard tissue such as teeth and bones, can be cut and ablated. The laser systems typically have output power levels up to the tens of watts, although systems with output power levels in the 10 milliwatt range have microbiocidal, tissue biostimulation, low-level light therapy, and other non-tissue-destructive applications.

A conventional laser system generally includes three primary components: a laser medium that generates the laser light, a power supply that delivers energy to the laser medium in the form needed to excite the same to emit coherent light, and an optical cavity or resonator that concentrates the light to stimulate the emission of laser radiation. Laser emissions can include ultraviolet wavelengths, visible light wavelengths, and infrared wavelengths, depending on the type of laser medium utilized (e.g., gas, chemical, dye, metal vapor, solid state, semiconductor, or others.)

For surgical laser applications requiring high output power, the lasers are often solid state types where the laser medium is comprised of a solid host crystalline or glass structure with an incorporated dopant material. In hard and soft tissue ablation applications, neodymium-doped yttrium aluminum garnet (Nd:YAG) lasers with an emission wavelength of 1.064 µm, erbium-doped yttrium aluminum garnet (Er:YAG) lasers with an emission wavelength of 2.94 µm, and holmium-doped yttrium aluminum garnet (Ho:YAG) lasers are frequently utilized. Furthermore, erbium chromium doped yttrium, scandium, gallium garnet (Er, Cr:YSGG) lasers have been utilized successfully in medical treatment applications. Other laser mediums utilizing gasses such as carbon dioxide, xenon, argon, excimer laser gases (such as noble gas halides), and copper vapor lasers have also been used with success.

During operation, an optical pump (e.g., a flash lamp) generates short-duration, intense, incoherent, full spectrum light to excite a laser medium (e.g., a doped solid host structure) to a population inversion state where atoms of an elevated energy state exceed those of a lower energy state with. In place of flash lamps, electrically powered diode lasers can also be utilized. The laser medium is disposed between two or more reflective mirrors that define an optical resonator. With each reflection off of the mirrors, the light is further stimulated by the optical pump, resulting in light amplification. One of the mirrors is a partial reflector, which allows some of the amplified light to exit the cavity as the laser emission and can also be referred to as an output coupler. The laser output is typically pulsed by such techniques as Q-switching, which can result in substantially higher instantaneous laser power output, although continuous or quasi-continuous operation is also possible.

Alternatively, a laser diode can also be utilized in medical treatment applications. Similar in operation to light emitting diodes, the laser diode is comprised of a p layer and an n layer, with an active, photon emitting layer in between. Like the solid state laser, there are one or more reflectors as well as an output coupler, which are incorporated into the semiconductor assembly, with electrical current providing the stimulus to reach the population inversion state.

A conventional laser apparatus suitable for surgical applications generally includes the aforementioned laser energy source coupled to a handpiece that can be manually operated by the practitioner. Due to the high power requirements and attendant safety concerns, the laser energy source is oftentimes located away from the operator and the patient. An extended waveguide, that is, a fiber optic cable, connects the laser energy source to the handpiece. In a basic implementation, the handpiece includes a tip that is in optical communication with the waveguide and the laser energy source. The tip directs the emitted laser on to a target tissue site, and varying shape configurations can yield different output profiles, including simple circular patterns. The laser emission can be directed at any angle that maximizes operator flexibility and comfort in accessing the target tissue site. The optical pathway can be offset from the connecting cable/handpiece axis using different reflector arrangements.

As briefly mentioned above, cutting and ablative efficacy largely depends upon the emitted wavelength and the absorptivity of that particular wavelength by the target tissue. Further, the intensity of the emission, along with the duration of the pulse, must be set to ensure that the tissue does not boil or vaporize (which can lead to greater injury and hemorrhaging). Following irradiation with a laser emission, the ablated tissue region is surrounded by a carbonization zone, a zone loosened by vacuoles, a coagulation zone, and a reversibly thermally damaged zone. The formation of the coagulation zone and the resultant hemostasis is advantageous in that tissue can be cut without bleeding.

In order to achieve the best results with the least amount of damage to the surrounding tissue, the laser emission parameters must be optimized for each clinical application. Most laser treatment apparatuses are therefore dedicated to one operation, though supplemental features that do not involve laser emissions are also known. For example, a water supply line and an air supply line have been incorporated into the handpiece to deliver water and air to the target tissue area. This cools the target tissue and removes debris. To further aid in the removal of debris, vacuum lines have also been incorporated. The use of water and air to improve efficacy has not been limited to these objectives, and an alternative cutting mechanism by which laser energy is directed to a distribution of atomized fluid particles located in a volume of space away from the targeted tissue site has been developed and disclosed in, for example, U.S. Pat. No. 5,741,247. The laser energy is understood to interact with the atomized fluid particles causing the same to expand and impart mechanical cutting forces onto the target surface.

To the extent multiple laser emissions are incorporated into a single laser system, existing systems such as those disclosed in U.S. Pat. No. 5,139,494 illustrate the use of a single laser catheter to the target tissue that is engaged to multiple sources of laser energy, each of which has a different therapeutic effect. The laser sources are separately activated, and while concurrent operation is indicated, each of the respective laser energy sources is configured to operate as an independent unit to known effect. Alternatively, some others have contemplated the adjustment of the laser source to enable the selective emission of laser energy at different wavelengths and durations.

Accordingly, there is a need in the art for an improved handheld laser treatment device with dual laser energy sources incorporated into the handpiece. There is also a need in the art for concurrent laser emissions in order to achieve enhanced treatment capabilities that exceed those of dual laser sources that operate independently. It would also be desirable for those laser emissions to be delivered along a common optical pathway.

SUMMARY OF THE INVENTION

In accordance with some embodiments, there is provided a handheld laser treatment device that combines the emissions of two separate laser energy sources into a common optical pathway for improved therapeutic effect. More particularly, the device comprises a housing having separate first and second laser sources disposed within the interior thereof. Laser energy emissions from the two internal laser sources can be individually or concurrently transmitted to a delivery tip of the device via a laser transmission path also defined within the interior of the housing. In some embodiments, the structural and functional features of the first and second laser sources, in concert with the unique architecture of the laser transmission path, is configured to provide efficacy and efficiency in the operation of the device within the spatial constraints of the lightweight, handheld housing thereof. In some embodiments, the laser transmission path is segregated into multiple segments and has various ancillary transmission components integrated therein. These components include first and second bending mirrors, a collimating lens, a focusing lens, and, optionally, a coupling fiber and a focusing mirror. In some embodiments, the lengths of the various segments of the transmission path in concert with the angular orientations and spatial relationships of such segments and the transmission components integrated therein relative to each other and to the first and second laser sources is specifically selected within the device to accomplish the aforementioned objectives, as will be described in more detail below.

Some embodiments of the invention include a compact, lightweight, hand-held laser treatment device comprising a housing and a first laser source disposed within the housing that is configured to facilitate the emission of a first laser beam having a first beam characteristic. In some embodiments, the laser treatment device also includes a second laser source which is at least partially disposed within the housing and is configured to facilitate the emission of a second laser beam having a second beam characteristic differing from the first beam characteristic. In some embodiments, the laser treatment device also comprises an elongate delivery tip defining a delivery axis and protruding from the housing, and a laser transmission path defined within the housing and configured to facilitate the transmission of one or both of the first and second laser beams to the delivery tip. The laser transmission path can comprise a plurality of discrete segments which are of prescribed lengths and a plurality of ancillary transmission components which are integrated into the segments at prescribed spatial relationships and angular orientations relative to each other and to the first and second laser sources. Further, the lengths of the segments, angular orientations, and spatial relationships of the ancillary transmission components relative to each other and to each of the first and second laser sources may be configured and arranged to enable the first and second beam characteristics of the first and second laser beams to be combined within at least one of the segments of the laser transmission paths forming coincident transmission of the first and second laser beams to the delivery tip.

In some embodiments of the invention, the treatment device includes a first laser source that comprises a high peak power, flash lamp pumped, solid state laser, and the second laser source comprises at least one of a high average power diode laser and a diode pumped fiber laser.

In some further embodiments, the treatment device comprises a first laser source that is configured to facilitate the emission of the first laser beam along a first laser source axis, and the second laser source is configured to facilitate the emission of the second laser beam along a second laser source axis. Further, the laser transmission path comprises a first segment defining a first axis which is coaxially aligned with the first laser source axis, a second segment defining a second axis which extends at a prescribed angle relative to the first axis, and a third segment defining a third axis which is coaxially aligned with the second laser source axis and extends at a prescribed angle relative to the second axis.

In some embodiments of the invention, the treatment device includes transmission components integrated into the laser transmission path that include a first bending mirror disposed between the first and second segments and is configured to facilitate directing the first laser beam from the first axis to and along the second axis. Further, a second bending mirror is disposed between the second and third segments and is configured to facilitate directing the first laser beam from the second axis to and along the third axis. Further, a focusing lens is disposed within the third segment along the third axis and is configured to focus the one or both of the first and second lasers beams toward the delivery tip.

In some embodiments, the treatment device further comprises a collimating lens disposed along the second laser source axis between the second laser source and the second bending mirror. Some embodiments include the first laser source separated from the first bending mirror by a prescribed first distance along the first axis. Further, the first and second bending mirrors are separated from each other by a prescribed second distance along the second axis, and the second bending mirror is separated from the focusing lens by a prescribed third distance along a portion of the third axis, and the second laser source is separated from the focusing lens by a prescribed fourth distance which is less than the total of the first, second and third distances. In some embodiments, the total of the first, second, and third distances is 25 mm or more.

In some embodiments, the delivery tip defines opposed input and output ends, with the delivery axis thereof being coaxially aligned with the third axis of the third segment, and the focusing lens is configured to focus one or both of the first and second laser beams onto the input end of the delivery tip.

In some embodiments of the invention, the transmission components are integrated into the laser transmission path and further include an elongate coupling fiber defining opposed input and output ends and disposed within the third segment along the third axis. The focusing lens is configured to focus one or both of the first and second lasers beams onto the input end of the coupling fiber, and a focusing mirror is disposed within the third segment along the third axis and is configured to facilitate the focusing of one or both of the first and second laser beams from the third axis to the delivery axis of the delivery tip. In some further embodiments, the delivery axis of the delivery tip extends at an angle of about 90° relative to the third axis.

In some embodiments of the invention, the treatment device comprises a coupling fiber that includes a bend comprising an arcuate contour, where a portion of the coupling fiber defining the output end extends at a prescribed angle relative to a linear portion of the third axis between the second bending minor and the focusing lens. Further, the delivery axis of the delivery tip extends at an angle of between about 90° to about 180° relative to the linear portion of the third axis.

Some embodiments of the invention include a compact, lightweight, hand-held laser treatment device comprising a first laser source configured to facilitate the emission of a first laser beam having a first beam characteristic, and a second laser source configured to facilitate the emission of a second laser beam having a second beam characteristic differing from the first beam characteristic. Further, the laser transmission path is configured to facilitate the transmission of one or both of the first and second laser beams from the treatment device. Furthermore, the laser transmission path comprises a plurality of discrete segments which are of prescribed lengths, and a plurality of ancillary transmission components which are integrated into the segments at prescribed spatial relationships and angular orientations relative to each other and to the first and second laser sources. Moreover, the lengths of the segments, angular orientations, and spatial relationships of the components relative to each other and to each of the first and second laser sources are configured and arranged to enable the first and second beam characteristics of the first and second laser beams to be combined within one of the segments of the laser transmission path forming coincident transmission of the first and second laser beams from the treatment device.

In some embodiments of the invention, the treatment device includes transmission components integrated into the laser transmission path that include a first bending mirror disposed between the first and second segments and configured to facilitate directing the first laser beam from the first axis to and along the second axis. Further, a second bending mirror is disposed between the second and third segments and is configured to facilitate directing the first laser beam from the second axis to and along the third axis. Further, a focusing lens is disposed within the third segment along the third axis and is configured to focus the one or both of the first and second lasers beams along the third axis within the third segment.

Some embodiments of the invention include a compact, lightweight, hand-held laser treatment device comprising an elongate housing, a delivery tip protruding from the housing, and a first laser source including a first laser source output disposed within the housing. The first laser source is configured to generate a first laser emission defined by a first beam characteristic, and a second laser source including a second laser source output is disposed within the housing. The second laser source configured to generate a second laser emission defined by a second beam characteristic different from the first beam characteristic. Further, a first transmission path is defined between the first laser source output and the delivery tip. The first transmission path has a first predetermined distance, and a second transmission path defined between the second laser source output and the delivery tip. The second transmission path has a second predetermined distance different from the first predetermined distance, and at least a portion of the first transmission path and the second transmission path are coaxial.

The first and second laser sources can be operated in concert to generate combined laser emissions that synergistically enhance tissue treatment. Furthermore, the efficacy of treatment with the dual laser emissions can be increased with the addition of a water spray that, for ablative forms of treatment, reduces ablation width, increases ablation depth, and reduces charring that harms the surrounding tissue. Synergistic bactericidal, bio-stimulation or wound healing, and pain reduction benefits from the concurrent operation of the two laser sources are also contemplated. By way of example, in accordance with some embodiments of the invention, one of the laser sources can primarily be used for ablation while having relatively limited bactericidal effects that weaken, but not entirely kill the bacteria. The second laser source, after the first laser source is pulsed, can generate another emission that kills the weakened bacteria, even though such emission is not in and of itself capable of killing normal bacterial. Furthermore, the effects of low-level laser therapy with one laser source in bio-stimulation applications can be increased with another laser source that generates pressure waves within the tissue. Pain reduction is also possible, in which the first laser source penetrates tissue and stuns nerve endings while the second laser source ablates tissue, thus eliminating pain signals that would otherwise result from treatment with the second laser source. A control system that selectively governs the emissions from the first and second laser sources can accomplish the aforementioned functions.

Some embodiments of the invention include a method for laser treatment of a target tissue site comprising applying a first laser emission defined by a first beam characteristic to the target tissue site, where the first laser emission alone has a first treatment effect on the target tissue site. The method may also include applying at least a second laser emission defined by a second beam characteristic to the target tissue site, where the second laser emission is applied within a predetermined time period of applying the first laser emission during which the target tissue site is subjected to the first treatment effect from the first laser emission. Further, the first laser emission and the second laser emission may comprise an additive treatment effect greater than the first treatment effect alone and the second treatment effect alone.

Some embodiments of the method include applying a first laser emission defined by a first beam characteristic to the target tissue site, and the first laser emission alone having a first treatment effect on the target tissue site. Some embodiments include applying at least a second laser emission defined by a second beam characteristic to the target tissue site, where the second beam characteristic is different from the first beam characteristic and has a second treatment effect different from the first treatment effect. Further, the second laser emission is applied within a predetermined time period of applying the second laser emission during which the target tissue site is subject to the first treatment effect from the first laser emission. Moreover, the first laser emission and the second laser emission may comprise a synergistic treatment effect different from both the first treatment effect and the second treatment effect independently with the first treatment effect and the second treatment effect being non-linearly enhanced by each other.

In some embodiments of the invention, the first laser emission and the second laser emission are combined and emitted from a single output of a treatment device. Some embodiments of the method include applying to the target tissue a third laser emission defined by a third beam characteristic and a third treatment effect. Further, in some embodiments, the first laser emission, the second laser emission, and the third laser emission have another synergistic effect different from the first treatment effect, the second treatment effect, and the third treatment effect independently.

In some embodiments of the invention, the first laser emission is applied to the target tissue site in pulses, and the second laser emission is applied to the target tissue site for a duration longer than the pulses of the first laser emission. In some embodiments, the first treatment effect comprises a pressure wave that weakens any bacteria on the target tissue site that includes a biofilm, where the bacteria are weakened by disruption of biofilm and bacterial membranes in response to the pressure wave. Further, the second treatment effect is induced by application infrared or ultraviolet radiation at the levels below the bacteria vitality threshold level for the applied radiation. Further, the synergistic treatment effect is at least one of neutralization, killing of the weakened bacteria, and reduction of inflammatory tissue conditions.

In some embodiments of the method, the first laser emission is generated from a solid state laser source comprising a high peak power flash lamp pumped solid state laser source, and the second laser emission is generated from a laser source comprising a diode laser source. In some embodiments of the method, first beam characteristic and the second beam characteristic each comprise output powers, where the output power corresponding to the second beam characteristic being greater than the output power corresponding to the first beam characteristic.

In some embodiments, the first laser emission and the second laser emission are applied to the target tissue site in pulses. In some further embodiments, the first treatment effect comprises a first ablation depth. In some further embodiments, the second treatment effect comprises a second ablation depth different from the first ablation depth, and the synergistic treatment effect comprises a third ablation depth greater than either one of the first ablation depth and the second ablation depth. In some other embodiments of the method, the second ablation depth is characterized by no ablation.

Some embodiments of the method include applying a fluid to the target tissue site. In some embodiments, the first treatment effect comprises application of a first level bio-stimulative energy to surrounding tissue of the target tissue site, and the second treatment effect comprises a treatment procedure not directly specified for bio-stimulation of the treatment site, where the synergistic treatment effect comprises a result of synergetic action of two treatment effects.

In some embodiments of the method, the second treatment effect is at least one of surgical cutting, removal of diseased tissue, and reduction of bacteria at the treatment site. Further, some embodiments of the method include a synergistic treatment effect that is at least one of a reduction of inflammatory effect, wound healing and tissue re-generation.

In some embodiments, the first beam characteristic and the second beam characteristic comprise output power, where the output power corresponding to the first beam characteristic and the output power corresponding to the second beam characteristic are at ablative levels. In some other embodiments of the method, the first beam characteristic and the second beam characteristic include output power, where the output power corresponding to the first beam characteristic and the output power corresponding to the second beam characteristic are at sub-ablative levels.

Some embodiments of the method for pain-free laser ablation of a target tissue site comprises applying a first laser emission to the target tissue site, where the first laser emission has a first treatment effect comprising analgesia inducing stunning of nerve endings. Further, the method includes applying a second laser emission to the target tissue site following the applying the first laser emission to the target tissue site. The second laser emission has a second treatment effect comprising ablation of the target tissue site, where the stunned nerve endings block transmission of pain signals otherwise initiated in response to the application of the second laser emission to the target tissue site. In some embodiments of the method, stunned nerve endings comprise stunned nerve endings in an area adjacent, proximate to and/or surrounding the target tissue site.

In some embodiments, the laser emission comprises a near infrared spectral wavelength. In some further embodiments, the first laser emission and the second laser emission are applied to the target tissue site in pulses. In some other embodiments of the method, the first laser emission and the second laser emission are combined and emitted from a single output of a treatment device.

Some embodiments of the method for laser treatment of a target tissue site comprise applying to the target tissue site a first laser emission pulse having a first wavelength, where the first laser emission pulse generates a pressure wave disruptive of membranes of bacteria present on the target tissue site. The method also includes applying to the target tissue site a continuous second laser emission having a second wavelength different from the first wavelength, the continuous second laser emission neutralizing the bacteria weakened from the pressure wave generated by the first laser emission pulse, where the continuous second laser emission comprises an output power level that is lower than an output power level of the first laser emission pulse. In some embodiments, the first laser emission pulse has a range of 3 micrometers and is generated from a high peak power flash lamp pumped solid state laser source.

Embodiments of the invention are best understood by reference to the following detailed description when read in conjunction with the accompanying drawings.

DETAILED DESCRIPTION OF THE INVENTION

Figure 1:
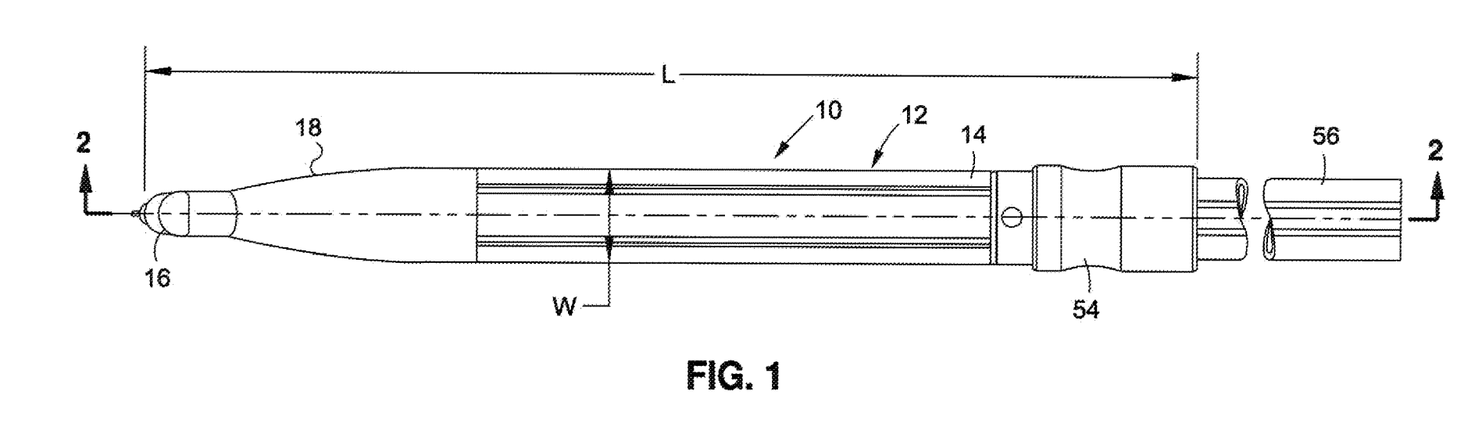
FIG. 1 is a top view of a hand-held treatment device constructed in accordance with one embodiment of the invention.
Figure 2:
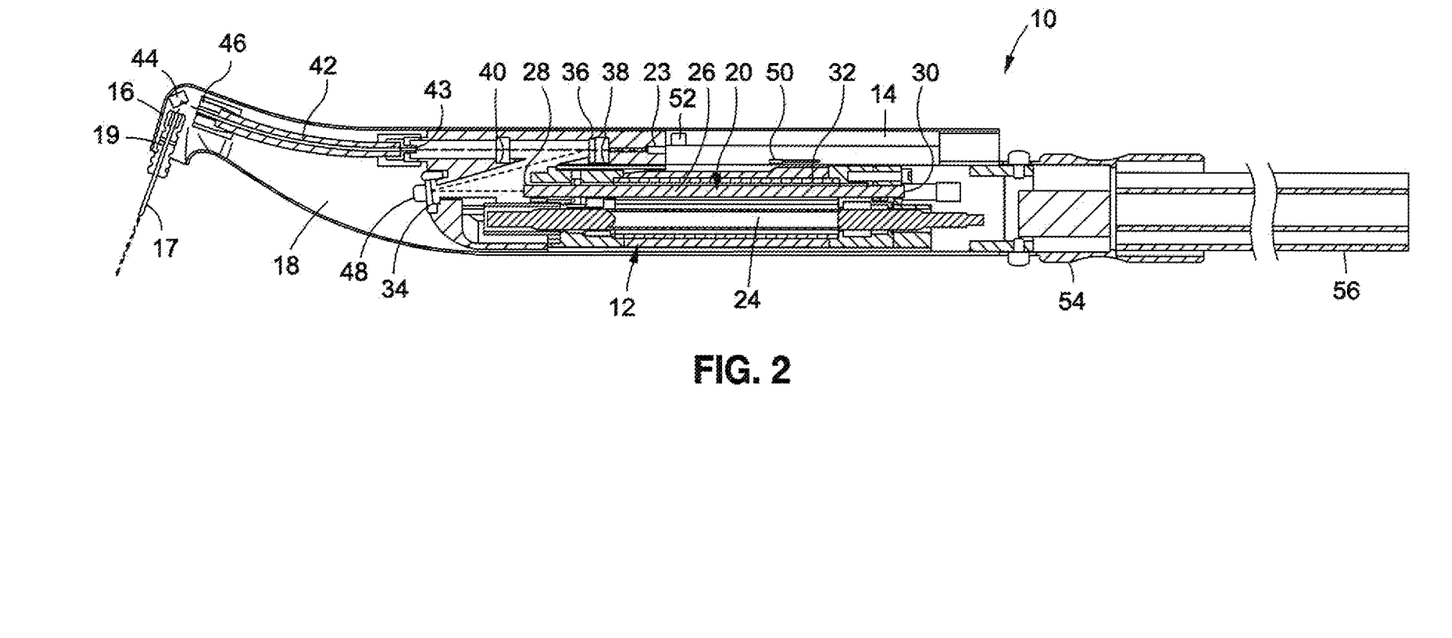
FIG. 2 is a cross-sectional view taken along line 2-2 of FIG. 1.

Referring now to the drawings for purposes of illustrating the various embodiments of the invention, and not for purposes of limiting the same, FIGS. 1 and 2 depict a hand-held, dual wavelength treatment device or hand-piece 10 constructed in accordance with one embodiment of the invention. In some embodiments, the device 10 comprises an elongate housing 12 which, as most easily seen in FIG. 2, showing a cross-sectional view taken along line 2-2 of FIG. 1, defines three separate regions, including a main body region 14, a distal head region 16, and a neck region 18. The neck region 18 can form a transition between the main body region 14 and the distal head region 16. In the embodiment shown in FIG. 2, the neck region 18 comprises a generally arcuate contour or profile. As will be discussed in more detail below, this arcuate contour is selected to cause laser energy to be transmitted from the output end 17b of an elongate delivery fiber or tip 17 (which directs the laser energy to a target surface) along a delivery axis DA which is defined by the delivery tip 17 and extends at a prescribed angle relative to one of three segments of a laser transmission path itself defined within the housing 12. However, in an alternative embodiment, which will also be described in more detail below, the housing 12 can be configured such that the delivery axis for the laser energy extends in coaxial alignment with one of the three segments of the laser transmission path.

In some embodiments of the invention, the device 10 comprises a housing 12 that is hollow, with the main body region 14 being tubular, and having a generally circular cross-sectional configuration. As viewed from the perspective shown in FIG. 1, in some embodiments, the housing 12 comprise an overall length L. In some embodiments, the overall length L can be in the range of from about 50 mm to about 300 mm. Further, in some embodiments, the main body region 14 can comprise a width or diameter in the range of from about 8 mm to about 40 mm. However, in any embodiment, the size of the housing 12, and in particular the diameter of the main body region 14 can be selected so as to be comfortably graspable in the hand of a medical clinician or practitioner, and easily moved or manipulated in the course of providing various treatment protocols as will be described in more detail below. Therefore, in other embodiments, the overall length L can be less than about 50 mm or greater than about 300 mm, and/or the body region 14 can comprise a width or diameter in the range of from less than 8 mm, or greater than about 40 mm.

Some embodiments of the invention include a plurality of laser sources coupled to the housing 12. For example, some embodiments of the invention include at least two laser sources coupled to the housing 12. In some embodiments of the invention, a first laser source 20 and a second laser source 22 can be coupled to the housing 12. In some embodiments, the device 10 can comprise a first laser source 20 that is disposed in its entirety within the interior of the main body region 14 of the housing 12. On the other hand, in some embodiments, only a portion of the second laser source 22, and in particular a delivery fiber 23 thereof, can extend into the interior of the main body region 14 of the housing 12. In this regard, in some embodiments, the remainder of the second laser source 22 can reside within a base unit (not shown) used in conjunction with the device 10. However, in accordance with a potential variant of the device 10, it is contemplated that, like the first laser source 20, in some embodiments, the entirety of the second laser 22 can reside within the interior of the main body region 14 of the housing 12.

In some embodiments of the invention, the first laser source 20 comprises a high peak power, flash lamp pumped, solid state laser comprising an elongate flash lamp 24 and elongate laser rod 26 which can extend in a side-by-side relation to each other. More particularly, in some embodiments, the flash lamp 24 and laser rod 26 can extend along respective spaced and generally parallel axes (i.e., a flash lamp axis and a laser rod axis), with the laser rod 26 being located proximate the flash lamp 24. In this instance, the traditional modes of operation of flash lamp pumped lasers can enable laser energy to be transmitted from the flash lamp 24 into the laser rod 26. Some embodiments of the invention include operational parameters for the first laser source 20 that are in a wavelength range of about 300 nm to about 3000 nm working in a free running or Q-switched mode. Further, in some embodiments, the pulse repetition rate of the first laser source 20 can range from a single shot mode up to about 1000 Hz. Further, some embodiments include a first laser source 20 with pulse durations from about 10 nsec to about 1 msec. In some embodiments, the beam divergence of the first laser source 20 can range from about 0.5 mrad to about 30 mrad.

Referring to the perspective view of FIG. 2, in some embodiments of the invention, the first laser source 20 further comprises an output coupler 28 disposed at one end of the laser rod 26 (i.e., the end disposed closest to the neck region 18 of the housing 12), and a reflector 30 disposed at the other end of the laser rod 26. Some embodiments of the invention also include an elongate flow tube or reflector 32 which accommodates portions of the flash lamp 24 and laser rod 26. In this regard, in accordance with known operational principles, the reflector 32 can facilitates transmission of laser energy from the flash lamp 24 to the laser rod 26. In some embodiments, the laser energy can then travel through the laser rod 26 to the aforementioned output coupler 28.

In some embodiments of the invention, the second laser source 22 can comprise a high average power diode laser or diode pumped fiber laser. In some further embodiments, the operational parameters of the second laser source 22 can comprise a wavelength range of about 300 nm to about 3000 nm. Further, in some embodiments, the second laser source 22 can operate in a continuous or a quasi-continuous mode. In some embodiments, the second laser source 22 pulse can operate with a repetition rate from a single shot mode up to about 1000 Hz. In some embodiments, the second laser source 22 pulse can operate with pulse durations from about 1 µsec up to a continuous mode. In some further embodiments, the second laser source 22 pulse can operate with an average output power of from about 10 mW up to about 100 W. In some embodiments of the invention, the second laser source 22 pulse can operate with a beam divergence from about 0.5 mrad to about 0.5 rad.

In some embodiments of the invention, as indicated above, whereas the flash lamp 24, laser rod 26, output coupler 28, and reflector 32 of the first laser source 20 each can reside within the interior of the main body region 14 of the housing 12, only the delivery fiber 23 of the second laser source 22 can extend into the interior of the main body region 14. In this regard, as also indicated above, in some embodiments, the remaining components of the second laser source 22 can reside within a base unit used in conjunction with the device 10. Further, the delivery fiber 23 can extend from the housing 12 to the base unit within a connector cable 56 between the device 10 and the base unit as will be described in more detail below.

Some embodiments of the invention include the device 10 including a first laser source 20 that, when activated, can facilitate the emission of a laser beam having a first beam characteristic. Similarly, in some embodiments, the second laser source 22, when activated, can facilitate the emission of a laser beam having a second beam characteristic. As utilized herein, the term "beam characteristic" refers to any one or combination of emission and operational parameters, including, but not limited to, wavelength, divergence, beam diameter, output power, pulse duration (whether periodic or continuous), duty cycle, pulse frequency, and any other parameters that can be adjusted to achieve different therapeutic effects. In this regard, it is also contemplated that the beam characteristics of laser beams generated by the first and second laser sources 20, 22 within the device 10 can differ from each other (i.e., at least one of the emission and operational parameters specified above will vary within the laser beams.)

In some embodiments of the invention, the device 10 can comprise the aforementioned laser transmission path defined within the housing 12 that can be provided with a unique architecture that allows the two separate emissions of the first laser source 20 and the second laser source 22 to be combined for output from the single delivery tip 17.

Figure 3:
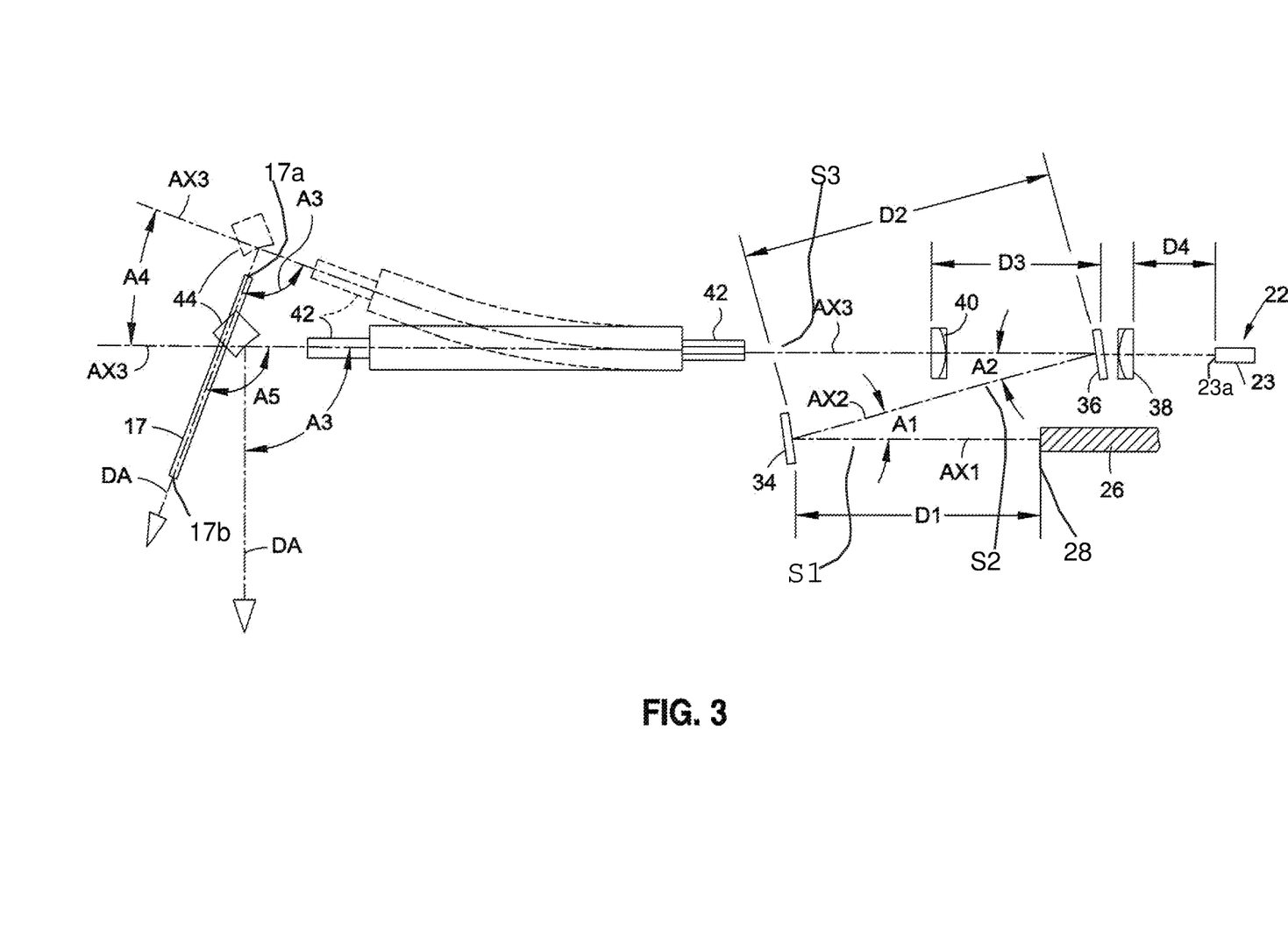
FIG. 3 is a schematic representation of the various internal components of the device shown in FIGS. 1 and 2, further illustrating several potential variants of the spatial relationships of such components relative to each other.

Referring to FIG. 3, illustrating a schematic representation of the various internal components of the device shown in FIGS. 1 and 2, further illustrating several potential variants of the spatial relationships of such components relative to each other, in some embodiments, the architecture of the transmission path further allows it to be accommodated within the interior of the hand-held housing 12, along with the entirety of the first laser source 20, and at least a portion of the second laser source 22. In some embodiments, upon reaching the delivery tip 17, laser energy can be transmitted along the delivery axis DA defined by the delivery tip 17, and subsequently to a treatment site.

It will be recognized by those having ordinary skill in the art that beam divergence is generally the inverse of the wavelength. As indicated above, the first laser source 20 and the second laser source 22 can have substantially overlapping output wavelength ranges, but in accordance with various embodiments of the invention, they are not operated at exactly the same wavelength (although the embodiments as described herein do not preclude the laser sources 20, 22 from operating at the same wavelength, and in some alternative embodiments, the laser sources 20, 22 can operate at substantially the same wavelength). Accordingly, based on the differing output wavelengths alone, in some embodiments, beam divergence is likewise understood to differ between the first laser source 20 and the second laser source 22. Beam divergence also depends on the particulars of the laser energy source, and further variability is introduced because of the differing laser types. For example, in some embodiments, the first laser source 20 can comprise a solid state configuration, while the second laser source 22 can comprise a diode configuration. Thus, per the foregoing discussion of the two laser sources, the first laser source 20 can comprise a beam divergence of from about 0.5 mrad to about 30 mrad, while the second laser source 22 can comprise a beam divergence of from about 0.5 mrad to 0.5 rad (i.e., the solid state laser has a lower divergence than the diode laser).

In accordance with some embodiments of the invention, laser beams with dissimilar beam characteristics characterized by different wavelengths and divergences can be effectively combined into a single final transmission path. For example, for a given single focusing element having a predetermined focal length, in some embodiments, this can be achieved by varying the respective distances between the emission outputs of the first and second laser sources 20, 22 and the focusing element (which will be described in more detail below). In some embodiments, a longer distance can be utilized for the first laser source 20, and for accommodating an increased distance within the spatial constraints of the hand-held housing 12. For example, some embodiments of the invention can include a transmission path that has a generally Z-shaped configuration in the device 10.

Referring to the perspective views shown in FIGS. 2 and 3, in some embodiments, the Z-shaped laser transmission path can include a linearly configured first portion or segment that defines a first axis AX1 coaxially aligned with the laser rod axis (which can also be referred to as the first laser source axis). Further, in some embodiments, the laser transmission path also includes a linearly configured second segment S2 which can define a second axis AX2 extending at a prescribed angle relative to the first axis AX1 of the first segment. In some embodiments, in addition to the first and second segments, the laser transmission path can include a third segment S3 defining a third axis AX3, at least a portion of which can extend linearly at a prescribed angle relative to the second axis AX2 of the second segment. As will be described in more detail below, in some embodiments of the invention, a portion of the third axis AX3 of the third segment S3 of the laser transmission path can include a linear configuration that can extend in a spaced, substantially parallel relation to the first axis of the first segment S1 thereof, and in a coaxial alignment with a second laser source axis of the second laser source 22 defined by at least a portion of the delivery fiber 23 (which extends into the interior of the main body region 14 of the housing 12.)

Some embodiments of the invention include a device 10 that is functional in several different operational modes. In some embodiments, the device 10 can include an operational mode where only the first laser source 20 is activated, resulting in the laser beam traveling along the first, second and third axes AX1, AX2, AX3 defined by the first, second and third segments of the laser transmission path, respectively, to the delivery tip 17. In a further embodiments of the invention, a second operational mode can include only the second laser source 22 activated, resulting in the laser beam traveling along the second laser source axis and thereafter the third axis AX3 of the third segment S3 of the laser transmission path to the delivery tip 17. In some other embodiments of the invention, the device 10 can include a third mode of operation, where the first and second laser sources 20, 22 are simultaneously activated, resulting in the laser beams being combined along the third axis AX3 of the third segment S3 of the laser transmission path prior to reaching the delivery tip 17.

In some further embodiments of the invention, the first laser source 20 and the output coupler 28 can be configured to facilitate the transmission of a laser beam from the laser rod 26 of the first laser source 20 in a direction along the first laser source axis into the first segment S1 of the laser transmission path and along the first axis AX1 thereof which is coaxially aligned with the first laser source axis. In some embodiments, the device 10 can include a first bending mirror 34 which can be integrated into the laser transmission path by locating at that end of the first axis AX1 of the first segment S1 of the laser transmission path disposed furthest from the output coupler 28.

In some embodiments, the first bending mirror 34 can be configured to direct a laser beam emission from the first laser source 20 (shown as being emitted from the laser rod 26 in FIG. 3) that can travel along the first laser source axis and through the first segment S1 of the laser transmission path along the first axis AX1 and into and through the second segment S2 of the laser transmission path along the second axis AX2. As illustrated in FIG. 3, in some embodiments, a prescribed distance D1 generally corresponding to the length of the first segment S1 of the laser transmission path can separate the output coupler 28 of the first laser source 20 from the first bending mirror 34. Further, as illustrated with arrows, in some embodiments, a prescribed angle A1 can be defined between the first and second axes AX1, AX2 of the first and second segments of the laser transmission path.

Some embodiments of the invention include a device 10 that further comprises a second bending mirror 36. Referring to FIG. 3, in some embodiments, a second bending mirror 36 can be integrated into the laser transmission path and located at that end of the second axis AX2 of the second segment S2 (which is opposite the first bending mirror 34). In some embodiments, the second bending mirror 36 can be configured to direct a laser beam emission from the first laser source 20 which travels along the second axis AX2 of the second segment S2 of the laser transmission path into the third segment S3 of the laser transmission path and along the third axis AX3 thereof toward the delivery tip 17. As also seen in FIG. 3, a prescribed distance D2 generally corresponding to the length of the second segment S2 of the laser transmission path separates the first and second bending mirrors 34, 36 from each other. Further, a prescribed angle A2 is defined between the second axis AX2 of the second segment S2 of the laser transmission path and a linearly configured portion of the third axis AX3 of the third segment S3 thereof. Moreover, this third segment S3 generally extends in a spaced, substantially parallel relation to the first axis AX1 defined by the first segment S1.

In some embodiments of the invention, the device 10 can comprise a second laser source 22 that is configured to facilitate the transmission of a laser beam along the second laser source axis which is coaxially aligned with the linearly configured portion of the third axis AX3 defined by the third segment S3 of the laser transmission path. Along these lines, as seen in FIGS. 2 and 3, in some embodiments, the device 10 can further comprise a collimating lens 38 which is interposed between the second laser source 22 and the second bending mirror 36 along the second laser source axis. In some embodiments, the collimating lens 38 functions in accordance with traditional principles well known in the art, effectively collimating and/or narrowing the laser beam generated by the second laser source 22 and facilitating transmission of the laser beam along the second laser source axis to and through the second bending mirror 36, and into the third segment S3 of the laser transmission path along the third axis AX3 thereof. In some embodiments, a prescribed distance D4 separates the collimating lens 38 from the second laser source 22. In some embodiments, this distance D4 is based on, and can be selectively varied in accordance with, the particular characteristics (e.g., beam divergence and wavelength) of the emission from the delivery fiber 23 of the second laser source 22.

Some embodiments of the invention include a device 10 that further comprises a focusing lens 40, an elongate coupling fiber 42, and a focusing minor 44 which are also integrated into the laser transmission path, and more particularly within the third segment S3 thereof. Further, in some embodiments, the focusing lens 40, the coupling fiber 42 and the focusing mirror 44 are arranged in the third segment S3 of the transmission path along the third axis AX3 thereof in series. Further, in some embodiments, the focusing lens 40 can be positioned between the second bending mirror 36 and the coupling fiber 42, and the coupling fiber 42 can be positioned between the focusing lens 40 and the focusing mirror 44. In some embodiments, as seen in FIGS. 2 and 3, the coupling fiber 42 has a slight arcuate contour imparted thereto which roughly coincides to that of the neck region 18 of the housing 12. In some embodiments of the invention, the device 10 can include a coupling fiber input 43 thereof that is disposed at that end of the coupling fiber 42 directed toward the focusing lens 40. Further, in some embodiments, the device 10 can be configured with a prescribed distance D3 that separates the second bending mirror 36 from the focusing lens 40.

In some embodiments, as illustrated in FIG. 3, a laser beam emission from the first laser source 20 can be directed by the second bending mirror 36 into the third segment S3 of the laser transmission path and/or a laser beam emission from the second laser source 22 which travels along the second laser source axis through the collimating lens 38 and second bending mirror 36. In some embodiments, each of the laser beams can substantially simultaneously travel along the third axis AX3 of the third segment S3 of the laser transmission path toward the delivery tip 17. For example, if the first and second laser sources 20, 22 are simultaneously rather than individually energized, laser beams generated thereby can be coincident along the third axis AX3 of the third segment S3 of the transmission path. In some embodiments, at least one laser beam can be passed through the focusing lens 40 which effectively focuses the at least one laser beam onto the coupling fiber input 43 of the coupling fiber 42. In some embodiments, after being transmitted into the coupling fiber 42 via the coupling fiber input 43, the one or more laser beams can be optically guided by the coupling fiber 42 to and through a protective window 46 (shown in FIG. 2) which is disposed on the end thereof opposite the end extending to the coupling fiber input 43. Further, in some embodiments, after passing through the protective window 46 of the coupling fiber 42, the one or more laser beams can be transmitted to the focusing mirror 44, which in some embodiments, can be configured to direct one or more laser beams to the input end 17a of the aforementioned delivery tip 17.

In some embodiments of the invention, in order to focus a laser beam generated by the first laser source 20 into the delivery tip 17 based on the anticipated operational parameters thereof and size limitations imposed by its housing 12, the device 10 can include a prescribed total distance represented by the sum of the distances D1, D2 and D3 along the corresponding first, second and third axes AX1, AX2 and AX3 of the first, second and third segments (S1, S2, S3) of the laser transmission path will separate the output coupler 28 from the focusing lens 40. More particularly, in some embodiments, based on the anticipated characteristics (e.g., beam divergence and wavelength) of the emission from the output coupler 28 of the first laser source 20, this total distance can be at least about 25 mm, and can be closer to about 50 mm.

As indicated above, in some embodiments of the invention, the shape and orientation of the focusing mirror 44 relative to the window 46 and the delivery tip 17 can result in the focusing mirror 44 effectively directing one or more laser beams transmitted thereto from the window 46 into the input end 17a of the delivery tip 17. In this regard, as seen in FIG. 3, a prescribed angle A3, which is in some embodiments is about 90°, can be defined between the delivery axis DA of the delivery tip 17 and that portion of the third axis AX3 which extends between the window 46 and the focusing mirror 44. In some embodiments of the invention, the delivery tip 17 can effectively guide the one or more laser beams along the delivery axis DA defined thereby to the distal output end 17b of the delivery tip 17, and ultimately to a treatment site proximate the output end 17b. Further, in some embodiments, the operative interface of the delivery tip 17 to the head region 16 of the housing 12 can be facilitated by a tip adaptor 19 (shown in FIG. 2) which accommodates a portion of the length of the delivery tip 17. In some embodiments, the tip adaptor 19 can be releasably engageable to the housing 12.

Referring to FIG. 3, in some embodiments of the invention, the device 10 can comprise a portion of the coupling fiber 42 that is bent to extend at a prescribed angle A4 relative to the linear portion of the third axis AX3 of the third segment S3 of the laser transmission path extending between the second bending mirror 36 and the coupling fiber input 43. In some embodiments, bending of the coupling fiber 42 can impart the aforementioned arcuate profile thereto. In the embodiment of the device 10 shown in FIGS. 1 and 2, the angle A4 can be about 20° which, as indicated above, roughly coincides with the arcuate profile of the neck region 18 of the housing 12. As further shown in FIG. 3, in some embodiments of the invention, the bend angle A4 imparted to the coupling fiber 42 can result in the delivery axis DA of the delivery fiber 17 extending at a prescribed angle A5 relative to the linear portion of the third axis AX3 of the third segment S3 of the laser transmission path extending between the second bending mirror 36 and the coupling fiber input 43. In some embodiments, this angle A5 can represent the sum of the angles A3 and A4. Thus, in some embodiments, due to the angle A3 being about 90°, and the angle A4 being about 20°, the angle A5 in the device 10 is about 110°. As a result, in some embodiments, the delivery tip 17, and hence the delivery axis defined thereby, likewise extends at an angle of about 110° relative to such linear portion of the axis of the third segment.

In some embodiments of the invention, the device 10 can be further outfitted with several sensors to assist in the function thereof within prescribed operational parameters. These sensors can include at least one air pressure sensor 48 which, as shown in FIG. 2, can be located proximate the first bending mirror 34 integrated into the laser transmission path. In some embodiments, during operation of the device 10, the air pressure sensor 48 can function as a safety feature to ensure that the delivery tip 17 is operatively coupled to the tip adaptor 19. In this regard, in some embodiments, if no delivery tip 17 is included in the device 10, the air pressure level within the interior of the housing 12 thereof can fall below a prescribed threshold which is otherwise maintained when the delivery tip 17 is interfaced to the tip adaptor 19. In some embodiments, if the pressure level falls below its prescribed level, the air pressure sensor 48 can function to prevent the activation of either of the first and second laser sources 20, 22.

In some embodiments of the invention, the device 10 can comprise a temperature sensor 50 which can be located proximate the first laser source 20. In some embodiments, the temperature sensor 50 can function as a safety feature to actively monitor the temperature of the device 10 resulting from the operation of one or both of the first and second laser sources 20, 22. In doing so, in some embodiments, the temperature sensor 50 can trigger an alarm or functional interrupt in the event the operating temperature exceeds a prescribed threshold. In some further embodiments, the sensors can include a smart sensor 52 which, as shown in FIG. 2, can be located proximate the second laser source 22. In some embodiments, during the operation of the device 10, the smart sensor 52 can function to verify the integrity of the optical path defined by the laser transmission path within the interior of the housing 12.

Referring to FIGS. 1 and 2, in some embodiments, the end of the main body region 14 of the housing 12 disposed furthest from the neck region 18 can be outfitted with a connector 54. In some embodiments, the connector 54 can be sized and configured to facilitate the operative interface of various components of the device 10 to the aforementioned base unit, including for example the first laser source 20, the various sensors 48, 50, 52, and/or a power source alone or in combination with a control unit residing within the base unit. In some embodiments, the operative interface can be facilitated by a cable 56 that is engageable to the connector 54. Further, assuming that the entirety of the second laser source 22 does not reside within the interior of the housing 12, in some embodiments, the connector 54 and cable 56 can also accommodate the delivery fiber 23 of the second laser source 22 which, as indicated above, can extend between the housing 12 and the remainder of the second delivery source 22 residing within the base unit.

As is further depicted in FIG. 3, in accordance with some embodiments of the invention, a variant of the device 10 can comprises a neck region that is not formed to have the arcuate contour or profile described above with respect to the neck region 18. As a result, in some embodiments, the coupling fiber 42 is likewise not bent at the aforementioned bend angle A4 of about 20° to assume the arcuate contour shown in FIG. 2, but rather has a linear configuration throughout the entire length. In the variant (shown as device 100 in FIGS. 4 and 5), by virtue of the coupling fiber 42 being straight, the third axis AX3 of the third segment S3 of the laser transmission path is linear or straight throughout the entire length thereof (i.e., between the second bending mirror 36 and the focusing mirror 44). In some embodiments, the variant can include one or more laser beams that, after passing through the protective window 46 of the straight coupling fiber 42, are transmitted to the focusing mirror 44. Further, in some embodiments, the focusing mirror 44 can be configured to focus the laser beam(s) to the input end 17a of the delivery tip 17 and along the delivery axis DA thereof. Further, as illustrated in FIG. 3, the absence of any bend angle within the coupling fiber 42, in conjunction with the shape and orientation of the focusing mirror 44 relative to the window 46 and the delivery tip 17, can result in the delivery axis DA of the delivery fiber 17 extending at the aforementioned prescribed angle A3 relative to the linear third axis AX3 of the third segment S3 of the laser transmission path. As indicated above, in some embodiments, the angle A3 can be about 90°.

Figure 4:
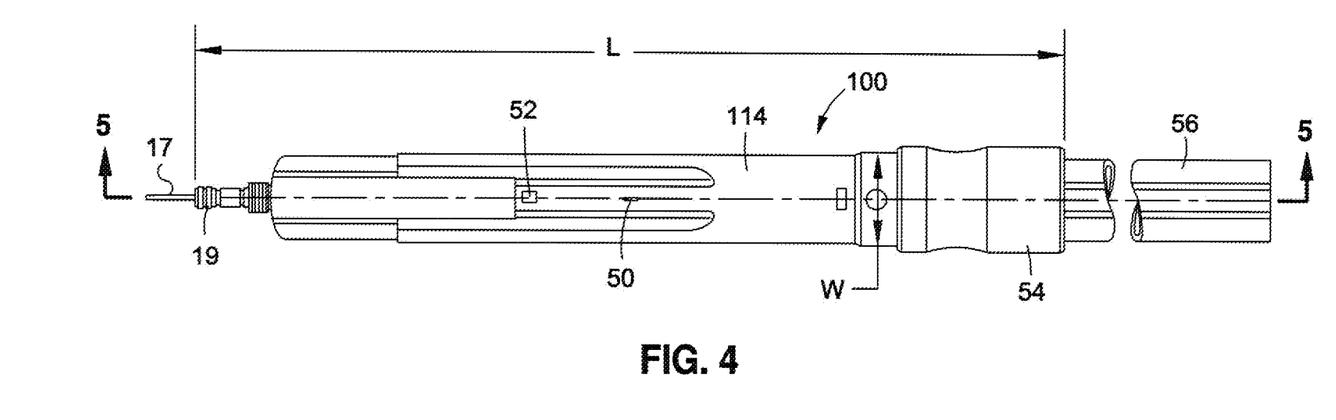
FIG. 4 is a top view of a hand-held treatment device constructed in accordance with another embodiment of the invention.
Figure 5:
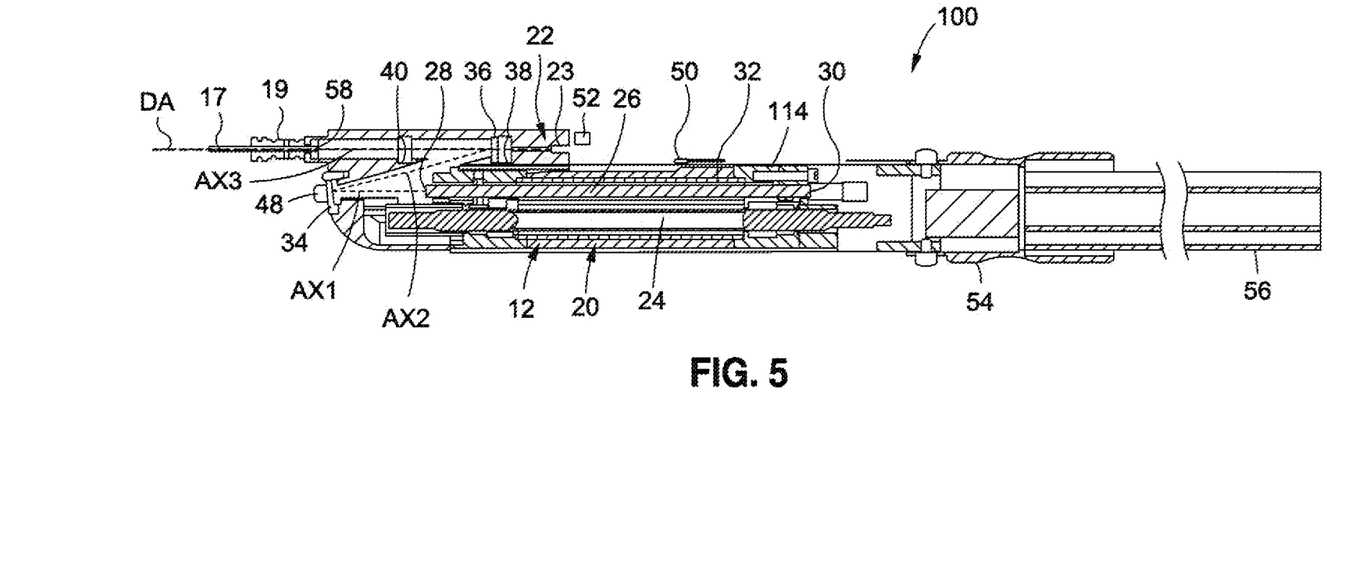
FIG. 5 is a cross-sectional view taken along line 5-5 of FIG. 4.

Referring now to FIGS. 4 and 5, FIG. 4 is a top view of a hand held treatment device constructed in accordance with a another embodiment of the invention, and FIG. 5 is a cross-sectional view taken along line 5-5 of FIG. 4. The device 100 bears a substantial measure of structural and functional similarity to the device 10 described above, with at least some distinctions between the devices 10, 100 being highlighted below. In this regard, those structural features common to both the devices 10, 100 are identified with the same reference numbers in FIGS. 1-5.

One of the primary distinctions between the devices 10, 100 pertains to the configuration of the housing 112 of the device 100 in comparison to that of the housing 12 of the device 10. In this regard, whereas in some embodiments, the housing 112 includes a main body region 114, it does not include the head and neck regions 16, 18 described above in relation to the housing 12. However, the main body region 114 of the housing 112 can be outfitted with the aforementioned connector 54 which is engageable to the cable 56 to facilitate the operative interface of device 100 to its corresponding base unit in the same manner described above in relation to the device 10.

Further, another primary distinction between the devices 10, 100 can include the absence or omission in the device 100 of the coupling fiber 42 and focusing mirror 44 described above in relation to the device 10. In this regard, in the device 100, the third axis AX3 of the third segment S3 of the laser transmission path can be linear or straight throughout the entire length thereof. More particularly, in the device 100, the third axis AX3 of the third segment S3 of the laser transmission axis can extend from the second bending mirror 36 to a delivery tip input 58 which is disposed at one of the opposed ends of the delivery tip 17 of the device 100. As such, in some embodiments, the delivery axis DA defined by the delivery tip 17 can be coaxially aligned with the third axis AX3 of the third segment S3 of the laser transmission path. Further, in some embodiments, by virtue of such coaxial alignment, the passage of one or more laser beams through the focusing lens 40 can effectively focus the same onto the delivery fiber input 58 (shown in FIG. 5). In some embodiments, from the delivery fiber input 58, the one or more laser beams can be transmitted to and along the delivery axis DA of the delivery tip 17, and subsequently therefrom to a treatment site proximate the distal end of the delivery tip 17. In some embodiments, as a result of the absence of the aforementioned head and neck regions 16, 18 in the housing 112, the air pressure, temperature and smart sensors sensor 48, 50, 52 are not embedded within the interior of the housing 112, but rather are exposed on corresponding or desired portions of the exterior surface thereof.

In some embodiments, in each of the treatment devices 10, 100, the lengths, angular orientations, and spatial relationships of the first and second segments (S1, S2) of the laser transmission path, the portion of the third segment S3 of the transmission path between the second bending mirror 36 and the focusing lens 40, the first and second bending mirrors 34, 36, the collimating lens 38 and focusing lens 40 relative to each other and to the first and second laser sources 20, 22, are the same. Further, as indicated above, in some embodiments, the lengths of the respective segments of the laser transmission path (as defined by the distances D1, D2, D3) in concert with the angular orientations and spatial relationships of such segments and the transmission components integrated therein relative to each other and to each of the first and second laser sources 20, 22 can be specifically selected within the devices 10, 100 to provide efficacy and efficiency in their operation within the spatial constraints of the lightweight, handheld housing 12, 112 thereof.

By way of example only and not by way of limitation, in the embodiments of the invention, the devices 10, 100 shown in FIGS. 1-5, and the distance D1 separating the output coupler 28 from the first bending mirror 34 (i.e., the length of the first segment S1 of the laser transmission path) can be about 20 mm. Further, in some embodiments, the angle A1 of the laser beam induced by the first bending mirror 34 (and hence the angular displacement between the first and second axes AX1, AX2 of the first and second segments of the laser transmission path) can be about 16°. Moreover, in some embodiments, the distance D2 separating the first and second bending mirrors 34, 36 from each other (i.e., the length of the second segment S2 of the laser transmission path) can be about 25.40 mm. Still further, in some embodiments, angle A2 of the laser beam induced by the second bending mirror 36 (and hence the angular displacement between the second axis AX2 of the second segment S2 of the laser transmission path and at least that portion of the third axis AX3 of the third segment S3 thereof which extends between the second bending mirror 36 and the focusing mirror 40) can also be about 16°. Still further, in some embodiments, the distance D3 separating the second bending mirror 36 from the focusing lens 40 can be about 13.16 mm, with a distance D4 separating the collimating lens 38 from the output end 23a of the delivery fiber 23 of the second laser source 22 being about 6.75 mm in some embodiments.

In addition to the foregoing, though not labeled with specificity in FIG. 3, in some embodiments, a distance separating the focusing lens 40 from the collimating lens 38 can be about 16 mm, thus making the total distance between the focusing lens 40 and the output end 23a of the delivery fiber 23 about 22.75 mm in some embodiments. Further, in some embodiments, a distance separating the focusing lens 40 from the coupling fiber input 43 of the coupling fiber 42 can be about 15 mm, with an un-bent length of the coupling fiber 42 being about 35 mm in some embodiments. Moreover, in some embodiments, the delivery tip 17 can include a length of about 17 mm, with a distance separating the point of intersection of the third axis AX3 with the focusing mirror 44 from the input end 17a of the delivery tip 17 being about 2.5 mm in some embodiments.

However, it is noted that the functionality of the device 10, 100 will not necessarily be unduly compromised by variations in the aforementioned dimensions corresponding to the laser transmission path and ancillary components integrated therein as specified with particularity above. In this regard, such variations can potentially be based on the particular length and/or width dimensions selected for the housing 12, 112 within those ranges also set forth above.

Some embodiments of the invention include a treatment device 10, 100 that can be coupled to a delivery system. For example, though not shown in the FIGS. 1-5, in some embodiments, either treatment devices 10, 100 can further be optionally outfitted with a delivery system (e.g., a water supply line and an air supply line) to facilitate the delivery of water and air to the target tissue area concurrently with the delivery of laser energy thereto from the delivery tip 17. In some embodiments, structural and functional features of such delivery systems in the context of laser handpieces can be found in U.S. Pat. Nos. 5,741,247, and/or 7,702,196, and/or 8,485,818, the disclosures of which are incorporated herein by reference in their entirety.

Some embodiments of the invention include a device 10 outfitted with more than two laser sources. More particularly, in some embodiments, the first laser source 20 (comprising for example the aforementioned high peak power, flash lamp pumped, solid state laser) configured to emit a laser beam having a first beam characteristic is used in combination with two or more additional laser sources (e.g., high average power diode lasers or diode pumped fiber lasers) configured to emit laser beams having beam characteristics differing from each other and from the first beam characteristic. In this alternative implementation, the emissions from the three or more laser sources included in the device 10 can be effectively combined into a single final transmission path.

In some embodiments, the combined emissions from two or more laser sources (e.g., the first laser source 20 and the second laser source 22) can comprise and/or create a synergistic effect beyond that which is understood to be possible from applying just one of laser source. In some embodiments, the first laser source 20 can comprise a solid state Er, Cr:YSGG laser operating at about 10 watts and about 20 pulses per second, and the second laser source 22 can comprise a diode laser operating at about 10 watts with a pulse width of about 50 ms. Notwithstanding these specific configuration values, it will be appreciated that such particulars can be modified to suit the application. As such, these configuration values are presented by way of example only and not of limitation.

Some embodiments of the invention include methods of use of the device 10, 100. For example, in some embodiments, the device 10, 100 can be used for ablation of soft and hard tissue. In some embodiments, laser energy can be emitted from the delivery tip 17, which can be understood to have wavelength and pulse duration parameters as described above and can be directed to a target site by a practitioner. According to well-recognized principles of laser surgery, the emitted laser beam can be understood to ablate the target tissue as well as impart secondary thermal, chemical, and mechanical effects on surrounding tissue as discussed above. Moreover, the laser energy can be absorbed by the targeted tissue and heated to an extent that it is vaporized or sublimated. Various surgical procedures call for such ablation to remove or otherwise restructure the targeted tissue.

In testing the functionality of the device 10 with biosimulation materials (e.g., various materials that simulate actual tissue), the combined laser energy from the first laser source 20 and the second laser source 22 was found to have greater ablation depth over a conventional, single laser source device that utilized the same solid state Er, Cr:YSGG laser. For example, a single pulse of the combined laser emission was found to have a tissue ablation depth of 147μ, which is understood to be approximately 58% deeper than the 93μ ablation depth exhibited by a single laser source. Thus, in some embodiments, the combining of the first laser source 20 and the second laser source 22 is understood to have a synergistic effect of improving the ablation rate. Moreover, the device 10 has been shown to include improved ablation precision and control, as well as improved haptic feedback. However, it was also discovered that the single pulse of the combined laser emission exhibited an ablation width of 128.5μ whereas the single solid state laser emission had a tissue ablation width of 88.5μ. In this regard, the dual laser source ablation width is approximately 45% wider over conventional single laser source ablation. It will be recognized that in many surgical applications, a narrower ablation width is desirable for improved precision, although this is not always necessarily the case.

In some embodiments of the invention, the efficacy of the laser treatment can be further improved by incorporating positive airflow and water spray. In some embodiments, the ablation width can be narrowed and ablation depth deepened by incorporating positive airflow and water spray. Furthermore, in some embodiments, the water spray can be understood to improve biocompatibility, as well as reduce incidents of charring. Some embodiments include the delivery of a water spray at about 1% air and about 20% water to the target tissue site. Under such conditions, the combined laser energy from the first laser source 20 and the second laser source 22 has been found to have a tissue ablation depth of about 203μ, and a substantially reduced tissue ablation width of 74μ. In comparison, a single laser source emission can utilize a water spray that exhibits an ablation depth of 160μ, and an ablation width of 65μ. Compared with conventional single laser source emissions combined with a water spray, embodiments of the invention comprising a dual laser source system can provide tissue ablation that is about 27% deeper and about 12% wider. Thus, some embodiments of the invention that utilize water spray can substantially improve efficacy, and can narrow ablation width, regardless of whether a single laser source or a dual laser source is used.

Figure 6:
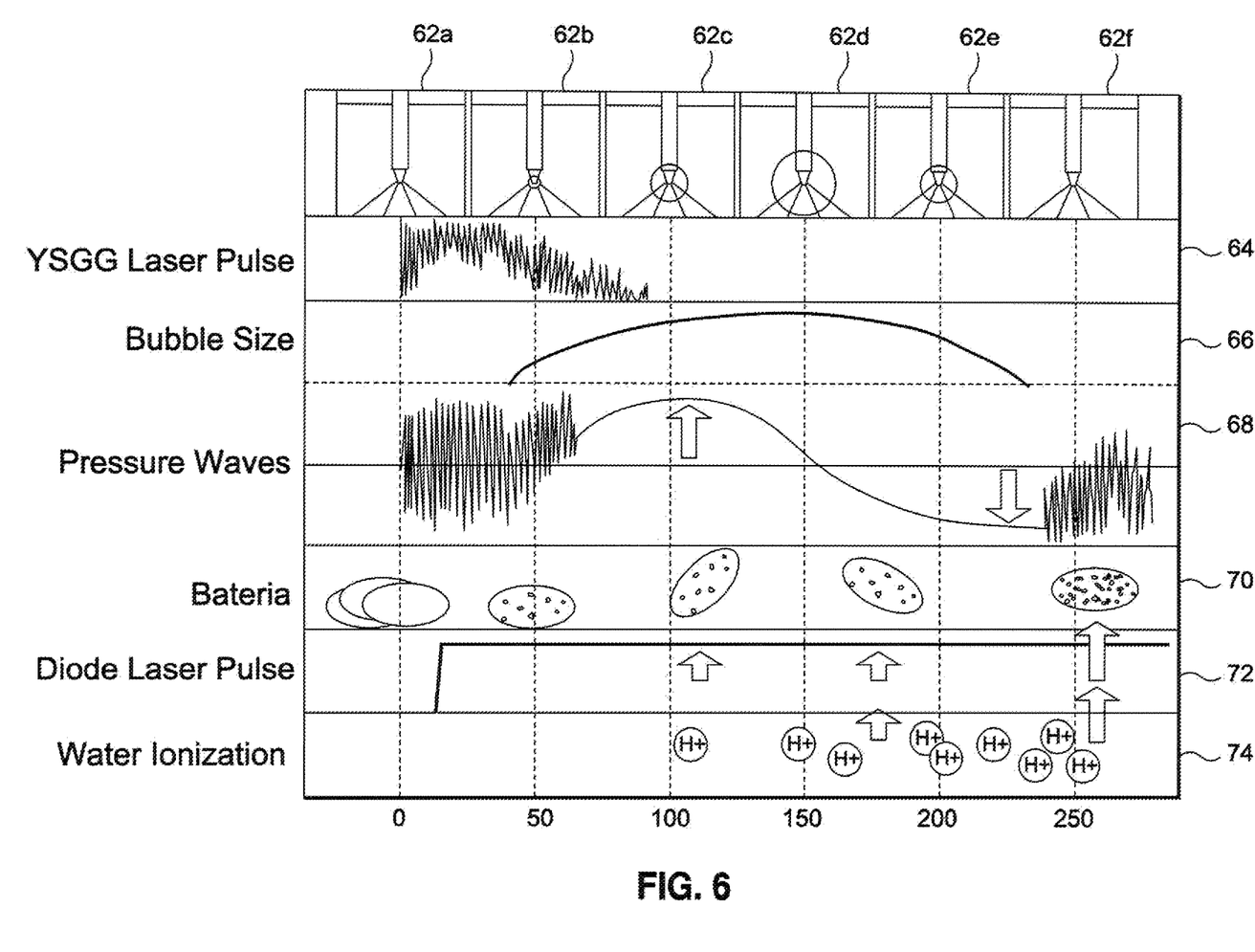
FIG. 6 is a diagram illustrating the combined synergistic antibacterial effects of the hand-held treatment device of some embodiments of the invention with a first laser source and a second laser source being pulsed across different stages of operation and includes graphical representations of waveforms of the laser pulses, a water bubble size, pressure wave, water ionization and the effects on bacteria.

Additional synergistic effects can be found in some embodiments. For example, some embodiments include a synergistic effect of applying laser light emitted from both the first laser source 20 and the second laser source 22 for killing and reduction of bacteria. For example, the diagram of FIG. 6 shows various waveform plots of the laser sources, resultant pressure waves, bacteria condition, bubble size, and water ionization states across different stages of operation of the device 10. A simplified representation of the laser output from the device 10 is also graphically illustrated, in sequence with the time/stages of operation. Some embodiments of the invention can be utilized for ablation via excitation of water molecules. For example, a first diagram 62a shows the tip 17 beginning to emit the laser beam, while a second diagram 62b shows the start of a water bubble being formed. It can be understood that the laser beam includes the emissions from the first laser source 20 (e.g., the Er, Cr: YSGG laser) though any other laser type that can be substituted. In accordance with at least one embodiment, the laser emission can comprise a wavelength of approximately 3 μm, and can be within a wavelength range of 2.70 to 3.00 μm), and is characterized by high water absorption.

In some embodiments of the invention, the second diagram 62b is a representation of what occurs at about the 50 μs mark. In some embodiments, the laser pulse can continue until about the 100 μs mark shown in a third diagram 62c. Further, in some embodiments, even after the laser pulse has stopped, the bubble can further increase in size until about the 150 μs mark shown in a fourth diagram 62d. In some embodiments, between about 0 μs and shortly before about 150 μs (as shown in a first plot 64) the laser pulse can be emitted, that in some embodiments, can result in a corresponding pressure or shock wave being generated as shown in a third plot 68. The formation and representative size of the bubble is shown in a second plot 66 according to some embodiments of the invention. Any other suitable pulsing parameters sufficient to generate this shock wave, or other desired effects in tissue, can be substituted.

The fourth plot 70 illustrates the condition of bacteria as it is exposed to the laser energy. Between about the 0 μs and about the 50 μs marks, the bacteria are in a fully active state, but with the increased exposure to the laser energy at approximately 50 μs, it begins to show signs of weakness. In some embodiments, the size of the water bubble can begin to decrease following the reduction of the laser energy from the maximum at the 150 μs mark. In some embodiments, the pressure wave can steadily declines through the 200 μs mark. In some embodiments, after the water bubble bursts, a fluctuating pressure wave on and around the 250 μs mark can be generated. In some embodiments, the shock or pressure wave can be understood to disrupt biofilm and the bacteria membranes for a short period of time.

In some embodiments, the second laser source 22 (e.g., the diode laser) can be activated in a substantially continuous mode shortly after 0 μs, and continuing past about the 250 μs mark (illustrated in a seventh plot 74). Further, in some embodiments, the water molecules in the spray start to become ionized, and the ionization level increases as the duration of its exposure to the second laser source 22 increases (as shown in a sixth plot 72). In some embodiments, the combination of the laser energy from the second laser source 22 and the ionized water can kill the bacteria that have been weakened through exposure to the laser energy from the first laser source 20. In particular, the relatively low power diode laser radiation, after penetrating through non-pigmented or slightly pigmented tissue, is understood to kill those wounded bacteria in some embodiments. Hence, some embodiments comprise and/or create a synergistic bactericidal effect that can be achieved with the operation of the two separate laser energy sources. In some embodiments, the combination can achieve results that one laser source standing alone, or two lasers operated sequentially are not able to achieve. It is understood that the diode laser itself would require substantially higher power levels to kill the same bacteria.

Some embodiments of the invention include devices 10, 100 that can comprise and/or create other synergistic effects of utilizing two separate laser energy sources for bio-stimulation and wound healing. In some embodiments, the effects of laser bio-stimulation, also referred to as low level laser thereby, are known in the art. The application of higher power, penetrating laser radiation utilizing diode laser modalities at ablative or non-ablative levels can apply to lower level laser radiation in surrounding tissue three-dimensionally through absorption and scattering. Moreover, the concurrent application of YSGG laser pulses also at ablative or sub-ablative power levels can generate pressure waves within water-rich tissue and can increase the effect of the aforementioned laser light therapy because of the mechanical stimulation of the tissue cells.

Some embodiments of the invention include devices 10, 100 that can comprise and/or create other synergistic effects of utilizing two separate laser energy sources for pain reduction during tissue ablation. In some embodiments, diode laser emissions in the near infrared spectrum have a penetrating wavelength, that is, the laser energy can enter biological tissue to a depth of approximately 1-2 cm (depending on tissue type and specific wavelength). In accordance with at least one embodiment of the invention, high power, short duration diode laser pulses can be applied to the tissue to generate stimuli within the peripheral nerve system that, in some embodiments, can block the transmission of pain signals. In some embodiments, this procedure can effectively stun the nerve endings for a short period of time, during which the YSGG cutting/ablating laser is pulsed. As such, there are no pain nerve signals that would otherwise be generated by the cutting/ablating operation, resulting in a painless treatment method.

In some embodiments of the invention, any of the aforementioned sequencing of driving the multiple laser energy sources can be variously implemented via signals from a control unit (not shown). In some embodiments, the control unit can include a general purpose data processor that executes pre-programmed instructions stored on an associated memory device that implement such control methods. In addition to the instructions for driving the laser energy sources, the control unit/data processor can further include instructions for user interface modules that receive configuration and operating inputs from the practitioner. Only one driving sequence has been illustrated, but due to the flexibility afforded in a software-based control system, any suitable laser energy delivery sequence can be substituted. Other types of sequencing are envisioned to have different therapeutic advantages that can be optimal for particular surgical operations.

In some embodiments of the invention, the control unit can measure readings from the various aforementioned sensors and trigger appropriate responses (up to and including terminating the laser emissions) after detecting hazardous operating conditions. In some embodiments, the readings from one or more of the sensors, including the air pressure sensor 48, the temperature sensor 50, and the smart sensor 52 described in further detail above, that are higher or lower than expected/normal readings can correspond to an unsafe state.

In some embodiments, the device 10 can include various features that enhance operator/practitioner as well as patient safety (features that are in addition to reactive safety measures that are taken in response to potentially dangerous conditions). For example, in some embodiments, with regard to the flash lamp of the first laser source 20 with a pump voltage at less than 600V at less than 300 W input power, potential exposure to high electric power can be minimized with the sealing of each of the aforementioned laser energy generating components within the housing 12.

It will be appreciated by those skilled in the art that while the invention has been described above in connection with particular embodiments and examples, the invention is not necessarily so limited, and that numerous other embodiments, examples, uses, modifications and departures from the embodiments, examples and uses are intended to be encompassed by the claims attached hereto. The entire disclosure of each patent and publication cited herein is incorporated by reference, as if each such patent or publication were individually incorporated by reference herein. Various features and advantages of the invention are set forth in the following claims.

What is claimed is:

1. A hand-held laser treatment device comprising:
   a housing,
   a distal head region,
   a first laser source, and
   a second laser source;
   wherein the housing includes the distal head region;
   wherein the first laser source is configured to emit a first laser beam having a first beam characteristic; and
   wherein the second laser source is configured to emit a second laser beam having a second beam characteristic differing from the first beam characteristic; and
   an air pressure sensor configured to function to prevent an activation of either of the first laser source and the second laser source based on a sensed air pressure.

2. The hand-held laser treatment device of claim 1, further comprising:
   a laser transmission path,
   a plurality of discrete segments, and
   a plurality of ancillary transmission components;
   wherein the laser transmission path is configured to transmit one or both of the first laser beam and the second laser beam;

wherein the laser transmission path comprises the plurality of discrete segments;
wherein the plurality of discrete segments are of prescribed lengths; and
wherein the plurality of ancillary transmission components are integrated into the plurality of discrete segments at prescribed spatial relationships and angular orientations relative to each other and to the first laser source and the second laser source.

3. The hand-held laser treatment device of claim 2,
wherein the laser transmission path comprises:
   a first segment,
   a first segment axis,
   a first laser source axis,
   a second segment,
   a second segment axis,
   a second laser source axis,
   a third segment, and
   a third segment axis;
wherein the first segment includes the first segment axis;
wherein the first segment axis is coaxially aligned with the first laser source axis;
wherein the second segment includes the second segment axis
wherein the second segment axis extends at a first angle relative to the first segment axis; and
wherein the third segment includes the third segment axis;
wherein the third segment axis is coaxially aligned with the second laser source axis; and
wherein the third segment axis extends at a second angle relative to the second segment axis.

4. The hand-held laser treatment device of claim 2,
wherein the plurality of ancillary transmission components includes:
   a coupling fiber,
   a focusing mirror, and
   a delivery tip;
wherein the focusing mirror is positioned in the distal head region; and
wherein the delivery tip protrudes from at least a portion of the housing.

5. The hand-held laser treatment device of claim 4,
wherein the laser transmission path comprises:
   a first segment,
   a first segment axis,
   a first laser source axis,
   a second segment,
   a second segment axis,
   a second laser source axis,
   a third segment, and
   a third segment axis;
wherein the first segment includes the first segment axis;
wherein the first segment axis is coaxially aligned with the first laser source axis;
wherein the second segment includes the second segment axis
wherein the second segment axis extends at a first angle relative to the first segment axis; and
wherein the third segment includes the third segment axis;
wherein the third segment axis is coaxially aligned with the second laser source axis;
wherein the third segment axis extends at a second angle relative to the second segment axis; and
wherein a portion of the third segment axis extends between an output end of the coupling fiber and the focusing mirror.

6. The hand-held laser treatment device of claim 5,
wherein the delivery tip comprises:
   a delivery axis;
wherein an angle between the delivery axis and the portion of the third segment axis is about 90 degrees.

7. The hand-held laser treatment device of claim 5,
wherein the focusing mirror is configured to direct the first laser beam and/or the second laser beam from an output end of the coupling fiber to an input end of the delivery tip.

8. The hand-held laser treatment device of claim 7,
further comprising a sensor configured to function to verify an integrity of an optical path within an interior of the housing.

9. The hand-held laser treatment device of claim 7,
further comprising a temperature sensor configured to function as a safety feature to actively monitor a temperature resulting from an operation of one or both of the first laser source and the second laser source.

10. The hand-held laser treatment device of claim 4,
wherein the plurality of discrete segments, the angular orientations, and a spatial relationship of the plurality of ancillary transmission components are configured and arranged to enable the first beam characteristic and the second beam characteristic to be combined within the laser transmission path forming a coincident transmission of the first laser beam and the second laser beam to the delivery tip.

11. The hand-held laser treatment device of claim 10,
wherein the first laser source is configured to emit the first laser beam along a first laser source axis; and
wherein the second laser source is configured to emit the second laser beam along a second laser source axis.

12. A hand-held laser treatment device comprising:
   a housing,
   a distal head region,
   a first laser source,
   a first laser source axis,
   a first beam characteristic,
   a second laser source,
   a second laser source axis,
   a second beam characteristic, and
   a laser transmission path;
wherein the housing includes the distal head region;
wherein the first laser source is configured to emit the first beam characteristic;
wherein the second laser source is configured to emit the second beam characteristic;
wherein the second beam characteristic is different from the first beam characteristic;
wherein the laser transmission path is configured to enable a transmission of one or both of the first beam characteristic and the second beam characteristic;
wherein the first laser source is configured to emit the first beam characteristic along the first laser source axis; and
wherein the second laser source is configured to emit the second beam characteristic along the second laser source axis; and
wherein the laser transmission path comprises:
   a first segment defining a first axis which is coaxially aligned with the first laser source axis;
   a second segment defining a second axis which extends at an acute angle relative to the first axis; and
   a third segment defining a third axis which is coaxially aligned with the second laser source axis and extends at an angle relative to the second axis.

13. The hand-held laser treatment device of claim 12, further comprising:

a delivery tip;

wherein the laser transmission path is configured and arranged to enable the first beam characteristic and the second beam characteristic to combine within one of the first segment, the second segment, or the third segment forming coincident transmission of the first beam characteristic and the second beam characteristic to the delivery tip.

14. The hand-held laser treatment device of claim 12, further comprising an air pressure sensor configured to function to prevent an activation of either of the first laser source and the second laser source based on a sensed air pressure.

15. The hand-held laser treatment device of claim 12, further comprising a sensor configured to function to verify an integrity of an optical path within an interior of the housing.

16. The hand-held laser treatment device of claim 12, further comprising a temperature sensor configured to function as a safety feature to actively monitor a temperature resulting from an operation of one or both of the first laser source and the second laser source.

17. A hand-held laser treatment device comprising:

a housing, a distal head region, a focusing lens, a coupling fiber, a first laser source, a second laser source, and a laser transmission path comprising:
  a first segment,
  a first segment axis,
  a first laser source axis,
  a second segment,
  a second segment axis,
  a second laser source axis,
  a third segment, and
  a third segment axis;

wherein the housing includes the distal head region;

wherein the first laser source is configured to emit a first laser beam having a first beam characteristic;

wherein the second laser source is configured to emit a second laser beam having a second beam characteristic differing from the first beam characteristic;

wherein the first segment includes the first segment axis;

wherein the first segment axis is coaxially aligned with the first laser source axis;

wherein the second segment includes the second segment axis;

wherein the third segment includes the third segment axis;

wherein the third segment axis is coaxially aligned with the second laser source axis;

wherein the focusing lens is configured to focus one or both of the first laser beam and the second laser beam into an input end of the coupling fiber; and wherein the coupling fiber is configured to optically guide one or both of the first laser beam and the second laser beam.

18. The hand-held laser treatment device of claim 17, wherein the second segment axis extends at a first angle relative to the first segment axis; and wherein the third segment axis extends at a second angle relative to the second segment axis.

* * * * *